United States Patent [19]
Tihon et al.

[11] Patent Number: 6,042,536
[45] Date of Patent: Mar. 28, 2000

[54] BLADDER SLING

[75] Inventors: Claude Tihon, Eden Prairie; Mark A. Rydell, Golden Valley; William P. Ryan, Minnetonka, all of Minn.

[73] Assignee: ContiMed, Inc., Eden Prairie, Minn.

[21] Appl. No.: 09/133,596

[22] Filed: Aug. 13, 1998

[51] Int. Cl.[7] .............. A61F 2/00; A61F 2/02; A61F 5/48

[52] U.S. Cl. .............. 600/37; 600/29; 600/30; 128/885

[58] Field of Search ............... 600/29, 30, 37; 128/885

[56] References Cited

U.S. PATENT DOCUMENTS

| | | | |
|---|---|---|---|
| 4,669,478 | 6/1987 | Robertson . | |
| 4,920,986 | 5/1990 | Biswas | 600/29 |
| 5,386,836 | 2/1995 | Biswas | 600/29 |
| 5,562,689 | 10/1996 | Green et al. | 606/151 |
| 5,785,640 | 7/1998 | Kresch et al. | 600/29 |
| 5,840,011 | 11/1998 | Landgrebe et al. | 600/30 |

OTHER PUBLICATIONS

*The Journal of Urology*, Jul. 1996, "Female Stress Urinary Incontinence Due to Intrinsic Sphincteric Deficiency: Recognition and Management", vol. 156, 3–17, Haab et al.

*Obstetrics & Gynecology*, "Suburethral Sling Release", Oct. 1995, vol. 86, No. 4, Part 2, pp.686–688, Brubaker.

*Anatomy and Pathophysiology of Pelvic Support*, Chapter 5, pp. 57–72, Wahle, et al.

*British Journal of Obstetrics and Gynaecology*, "A follow up of silastic sling for genuine stress incontinence", Feb. 1995, vol. 102, pp. 143–147, Chin et al.

*International Urogynecology Journal*, "Pubovaginal Slings: Past, Present and Future", 1997, pp. 358–368, Sarver et al.

*Primary Examiner*—Cary O'Connor
*Assistant Examiner*—Navin Natnithithadha
*Attorney, Agent, or Firm*—Nikolai, Mersereau & Dietz, P.A.

[57] ABSTRACT

A sling for supporting the urethra and neck of the bladder to prevent urinary incontinence is disclosed. The sling is designed to provide sufficient support to inhibit the unintended flow of urine, yet stretch in a controlled fashion so that the bladder can be voided at approximate times.

33 Claims, 4 Drawing Sheets

BLADDER SLING

BACKGROUND OF THE INVENTION

I. Field of the Invention

This invention relates generally to the treatment of urinary incontinence. More specifically, this invention relates to our improved sling that can be surgically implanted to support the urethra and bladder neck to mitigate the involuntary discharge of urine from the bladder.

II. Description of the Prior Art

Urinary incontinence is a common problem, especially in women. It is estimated that there are over 13 million individuals with urinary incontinence in the United States, of which about 85% are women. Stress urinary continence is a condition in which the patient leaks urine when a sudden increase in his or her abdominal pressure occurs. This increase in abdominal pressure can result from many routine daily activities such as laughing, sneezing, walking, or getting up from a chair. The increase in abdominal pressure (causes an increase in pressure in the bladder. When the pressure in the bladder is sufficiently great to overcome urethral sphincter leakage will occur.

Various treatments have been provided for stress urinary incontinence. For over 100 years, surgeons have used suburethral sling procedures to treat severe or refractory genuine stress incontinence. This preprocedure, sometimes referred to as pubovaginal sling procedure, is used to treat urinary stress incontinence by creating a support to the urethra and bladder neck complex. Providing this support serves to increase the urethral closure pressure during stress to mitigate the involuntary loss of urine. In this surgical procedure, a sling hanging from and secured to the pubo-abdominal side is used to support the urethra from below.

Traditionally the materials used to create the sling include excised native retus fascia and fascia lata from the patient. More recently, chemically treated cadaveric fascia lata has been used. Some synthetic materials have also been used. These included woven sheets made of polypropylene, Dacron, and other flexible but non-elastic material. Synthetic slings have also been coated with collagen products, such as Protegen, which is marketed by Boston Scientific Corporation. Protegen is a stiff woven material coated with collagen which is intended to provide faster or better tissue integration into the sling material.

Though the pubovaginal sling procedures have been effective in returning continence to women, there is a common and persistent problem of high rates of prolonged urinary retention after surgery. This problem often requires the patients to perform self-catheterization and can also lead to secondary detrusor instability. Various techniques have been devised in an effort to overcome such problems. These techniques generally allow the final ligature a substantial amount of free-play by adjusting the sling tension to reduce urinary retention and provide continence. However, these techniques require great skill and increase the difficulty of an otherwise very effective surgical procedure.

SUMMARY OF THE INVENTION

The present invention relates to a new sling which reduces the overall difficulty in tension adjustment by providing the patient with a more normal and physiological support. Specifically, the material from which the sling is made is; elastic in contrast to other synthetic materials previously used. This elasticity approximates the elasticity of surrounding tissue supporting the urethra and bladder neck complex. This elasticity is sufficient to accommodate the normal up and down movements of the urethra and bladder neck complex. Thus, slings made in accordance with this invention do not overly compress the urethra. Nor do they compress the urethra abruptly and totally to cause urinary retention as is the case with slings made of non-elastic material.

The present invention also includes length limiting means for the elastic sling. Thus, the sling inhibits the excessive decent of the bladder neck during stress conditions. This is important because, under stress, the bladder neck can drop. If the dropping of the bladder neck is rot restricted and the neck is allowed to descend too far, urine leakage can occur as a result of the hyper mobility of the bladder neck. Thus, the present invention, by providing an elastic sling with a length expansion limitation, reduces the undesirable side effect of urinary retention by not abruptly and completely occluding the urethra in normal bladder movements, but prevents excessive bladder neck decent to minimize urine leakage in stress situations.

The elasticity of the sling of the present invention provides additional benefits as well. The medical literature reports that one side effect of sling procedures performed in the prior art can be urethral tissue erosion. This erosion can be the result of prolonged and tight contact of a relatively stiff synthetic material with the urethra. The present invention, by providing a sling made of an elastic material which more closely approximates the surrounding tissue's softness, reduces the amount of injury to the urethra as compared to the stiffer materials used in the prior art.

BRIEF DESCRIPTION OF THE DRAWINGS

A greater understanding of the present invention can be derived from a reading of the following detailed description of the invention in conjunction with the drawings which also form a part of this specification. In the drawings, like parts of the various embodiments have been given like numbers.

DETAILED DESCRIPTION OF THE INVENTION

Figure 1:
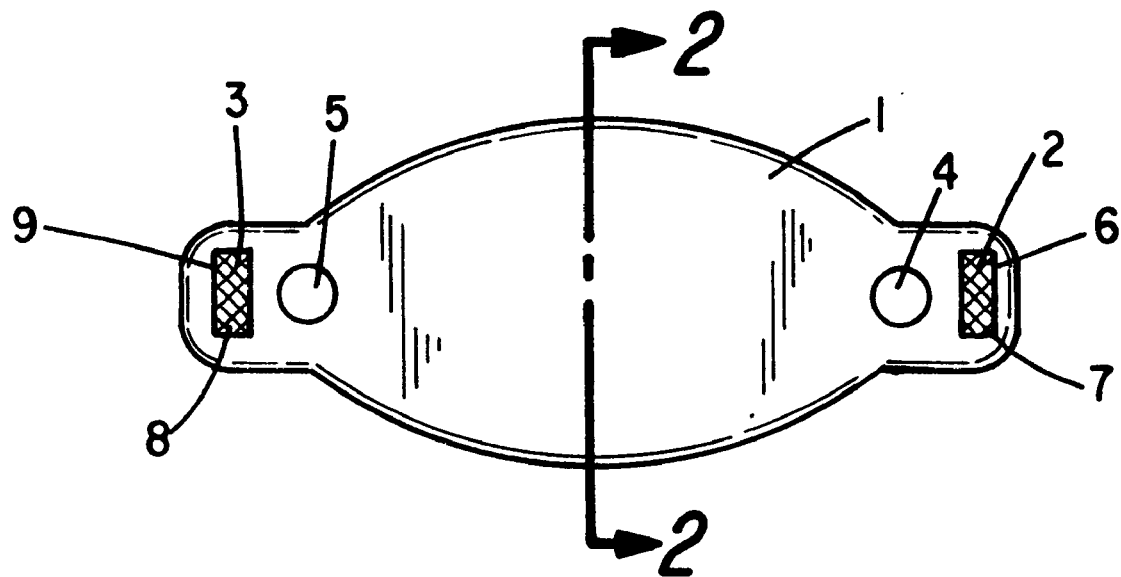
FIG. 1 is a top view of a sling made in accordance with the present invention.
Figure 2:
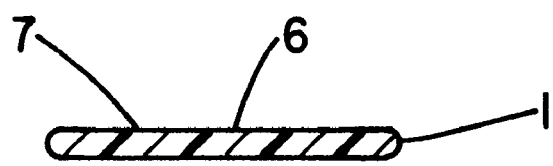
FIG. 2 is a cross-sectional view through line 2—2 in FIG. 1.
Figure 3:
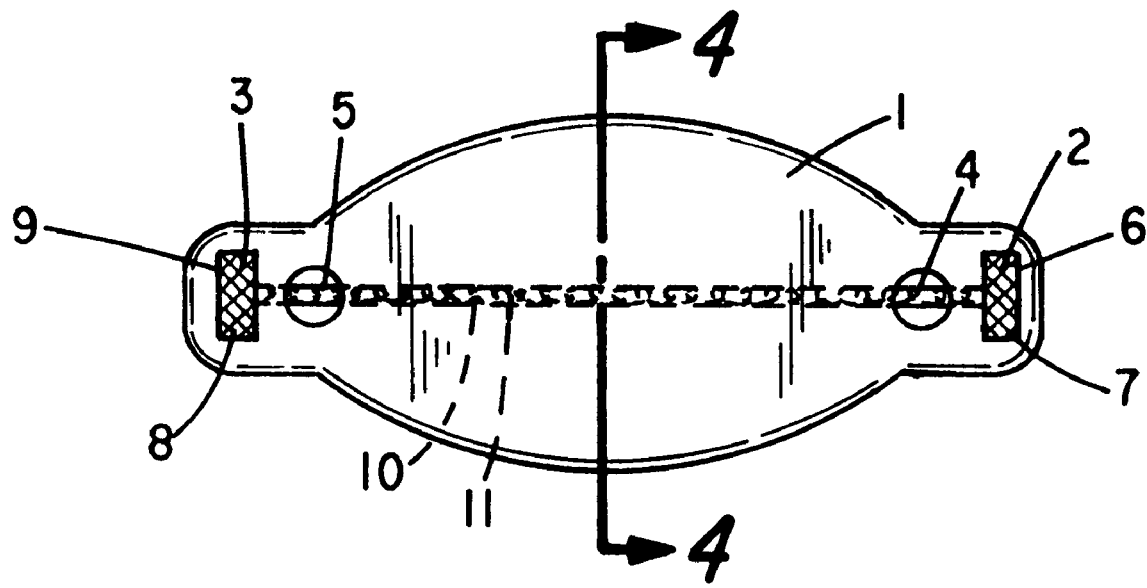
FIG. 3 is a top view of a second embodiment of a sling made in accordance with the present invention.
Figure 4:
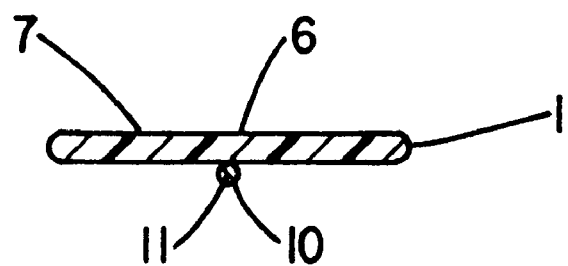
FIG. 4 is a cross-sectional view through line 4—4 in FIG. 3.
Figure 5:
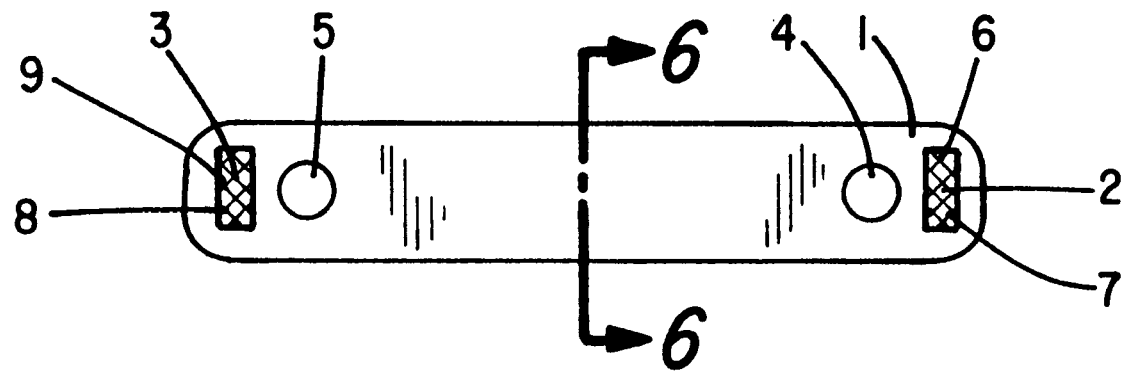
FIG. 5 is a top view of a third embodiment of a sling made in accordance with the present invention.
Figure 6:
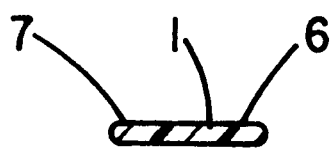
FIG. 6 is a cross-sectional view through line 6—6 in FIG. 5.
Figure 7:
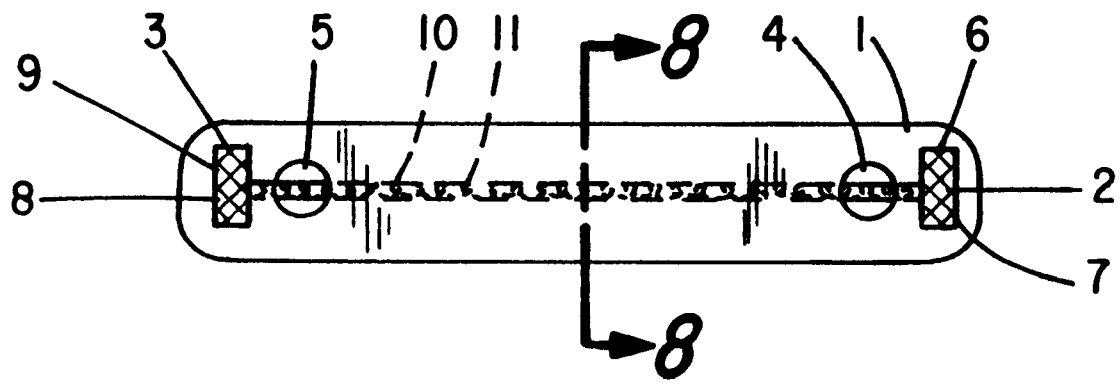
FIG. 7 is a top view of a sling made in accordance with a fourth embodiment of the present invention.
Figure 8:
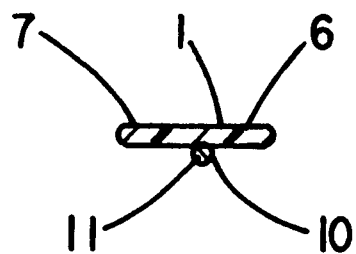
FIG. 8 is a cross-sectional view through line 8—8 in FIG. 7.

The drawings show four different embodiments of the invention. Each embodiment includes a support 1, a pair of suture anchors 2 and 3, a pair of relief holes 4 and 5, and at least four sutures 6, 7, 8 and 9. The support 1 is preferably made of a synthetic biocompatible, elastic material. The elasticity of the material should approximate that of the tissue normally surrounding the urethra. One such material is silicone. When silicone is used, the support 1 will generally be non-porous and no tissue integration into the support 1 will occur. Alternately, the support 1 can be made of a woven or porous material to promote tissue integration into the support 1. The support 1 can also be coated to inhibit infection or inflammation or to promote tissue repair, tissue growth, and lubricity. The support 1 can have a generally rectangular shape as shown in FIGS. 5 and 7. To provide for better distribution of tension to the urethra, to minimize tissue damage, and to minimize erosion, the support 1 can also have an oval shape as shown in FIGS. 1 and 3.

The suture anchors 2 and 3 can be made of a variety of materials including metal or of a semi-rigid thermoplastic material. More specifically, the suture anchors 2 and 3 can be made of stainless steel or polypropylene, polyethylene, polytetrafluoroethylene, or nylon.

The suture anchors 2 and 3 serve to reinforce the ends of the support 1. The suture anchors 2 and 3 also improve suture attachment to the support 1. The suture anchors 2 and 3 also provide more even distribution of pull force to the support 1 as it supports the urethra.

The relief holes 4 and 5 are provided to increase the overall stretchability or elasticity of the support 1. The relief holes may not be needed if the material from which support 1 is made sufficiently elastic. The size and the number of relief holes can be modified to adjust the stretchability or elasticity of the support 1.

The sutures 6–9 are used to fix the sling to the abdominal tissue, pubis symphysis or any other suitable tissue or support to anchor the sling in place. A shorter support 1 can be combined with longer sutures extending from the ends of the support 1 to provide the surgeon with more options for securing the sling in place.

The embodiments shown in FIGS. 3–4 and 7–8 include additional structures for limiting the overall elasticity of the sling. Specifically, these embodiments include a flexible, stretchable sheath 10 extending laterally across and secured to the underside of the support 1. The sheath 10 is both thin and very elastic as compared to the support 1. Encased within the sheath 10 is a monofilament string 11, the opposite ends of which are secured to the suture anchors 2 and 3. The monofilament string 11 is "precoiled" by a heat-set operation. In this configuration, the monofilament string serves as a brake to limit how much the sling can stretch. As the sling stretches, the monofilament string 11 uncoils. When the string 11 is fully uncoiled, the sling can stretch no further. The sheath 10 is placed on the underside of the support 1 away from the urethra so it does not irritate the urethra. The sheath 10 ran be made of silicone or some other elastomeric material which prevents tissue ingrowth that could interfere with the coiling or uncoiling of the string 11. Alternatively, the string 11 could be embedded in the material from which support 1 is made so that the sheath 10 is integral with the support 1.

As indicated above, the present invention is used to treat urinary incontinence by supporting the urethra and neck of the bladder. The device is surgically implanted so that the support 1 is beneath and in contact with the area to be supported. The surgeon sutures the device to abdominal tissue, pubis symphysis, other tissue or support suitable to fix the sling in place. The sling, when so positioned, flexibly supports the urethra and neck of the urethra. Sufficient support is provided to inhibit unintended discharge of urine. Yet, there is sufficient elasticity so that prolonged urinary retention is not a problem and the bladder can be voided at the approximate time.

What is claimed is:

1. For the treatment of urinary incontinence by supporting the urethra and neck of the bladder, a sling comprising:
    a) a support made of a stretchable non-porous material to limit tissue integration into the support;
    b) first and second suture anchors positioned at opposite ends of the stretchable support; and
    c) sutures cooperating with said suture anchors to fix the stretchable support in place.

2. The sling of claim 1 wherein said material from which said support is made is a synthetic, biocompatible, elastic material.

3. The sling of claim 2 wherein the elasticity of said material approximates that of human tissue.

4. The sling of claim 2 wherein said material is silicone.

5. The sling of claim 2 wherein said material is porous.

6. The sling of claim 2 wherein said material is treated to inhibit infection.

7. The sling of claim 2 wherein said material is treated to inhibit inflammation.

8. The sling of claim 2 wherein said material is treated to promote tissue ingrowth.

9. The sling of claim 2 wherein said material is lubricious.

10. The sling of claim 2 wherein said material is treated to improve lubricity.

11. The sling of claim 1 wherein said support is rectangular in shape.

12. The sling of claim 1 wherein said support is generally oval in shape.

13. The sling of claim 1 further including at least one relief hole through said support.

14. The sling of claim 13 wherein the elasticity of the support is a function of the size of said relief holes.

15. The sling of claim 13 wherein the elasticity of the support is a function of the number of said relief holes.

16. The sling of claim 1 further including a flexible sheath extending laterally across said support, and a string extending within said sheath, said string having a first end coupled to said first suture anchor and a second end coupled to said second suture anchor.

17. The sling of claim 16 wherein said sheath is integral with said support.

18. The sling of claim 16 wherein said sheath is secured to the underside of said support.

19. The sling of claim 16 wherein said string limits how much the sling can stretch.

20. The sling of claim 16 wherein said string is a monofilament.

21. The sling of claim 20 wherein said string is pre-coiled by a heat set operator.

22. The sling of claim 1 wherein said sutures are made of an elastic material.

23. For the treatment of urinary incontinence by supporting the urethra and neck of the bladder, a sling comprising:
    (a) a support;
    (b) first and second suture anchors positioned at opposite ends of the support; and
    (c) stretchable sutures cooperating with said suture anchors to hold the support within a desired range of motion.

24. A device for supporting the urethra and bladder neck to treat urinary incontinence, comprising an elongated, flexible elastic support member having first and second ends, said ends adapted for connection to a portion of the anatomy with the support member spanning the bladder neck.

25. For the treatment of urinary incontinence by supporting the urethra and neck of the bladder, a sling comprising:

(a) a stretchable support including at least one relief hole through said support;
(b) first and second suture anchors positioned at opposite ends of the stretchable support; and
(c) sutures cooperating with said anchors to fix the stretchable support in place.

26. The sling of claim 25 wherein the elasticity of the stretchable support is a function of the size of said relief holes.

27. The sling of claim 25 wherein the elasticity of the stretchable support is a function of the number of said relief holes.

28. The sling of claim 25 further including a flexible sheath extending laterally across said support, and a string extending within said sheath, said sling having a first end coupled to said first suture anchor and a second end coupled to said second suture anchor.

29. The sling of claim 28 wherein said sheath is integral with said support.

30. The sling of claim 28 wherein said sheath is secured to the underside of said support.

31. The sling of claim 28 wherein said string limits how much the sling can stretch.

32. The sling of claim 28 wherein said string is a monofilament.

33. The sling of claim 32 wherein said string is pre-coiled by a heat set operator.

* * * * *